United States Patent [19]

Vanlerberghe et al.

[11] 4,217,344
[45] Aug. 12, 1980

[54] COMPOSITIONS CONTAINING AQUEOUS DISPERSIONS OF LIPID SPHERES

[75] Inventors: Guy Vanlerberghe, Commune de Villevaude; Rose-Marie Handjani, Paris, both of France

[73] Assignee: L'Oreal, Paris, France

[21] Appl. No.: 865,499

[22] Filed: Dec. 29, 1977

Related U.S. Application Data

[63] Continuation-in-part of Ser. No. 700,038, Jun. 25, 1976, abandoned.

[30] Foreign Application Priority Data

Jun. 23, 1976 [BE] Belgium ................................ 168219
Nov. 15, 1977 [FR] France ............................... 77 34249

[51] Int. Cl.$^2$ ........................ A61K 7/44; A61K 7/021
[52] U.S. Cl. ..................................... 424/60; 252/316;
252/522 A; 424/19; 424/31; 424/32; 424/36;
424/38; 424/59; 424/62; 424/63; 424/280;
426/89
[58] Field of Search .................... 252/316; 424/26, 31,
424/32, 36, 38, 351, 60, 63

[56] References Cited

U.S. PATENT DOCUMENTS

| | | |
|---|---|---|
| 1,959,930 | 5/1934 | Schmidt et al. ................. 252/351 X |
| 2,853,423 | 9/1958 | La Via ................................. 424/60 X |
| 2,949,403 | 8/1960 | Andreadis et al. ................ 424/60 X |
| 3,041,289 | 6/1962 | Katchen et al. ...................... 252/316 |
| 3,630,920 | 12/1971 | Freifeld et al. .......................... 252/90 |
| 3,686,701 | 8/1972 | Charle et al. ...................... 424/32 X |
| 3,932,657 | 1/1976 | Rahman ........................... 424/365 X |
| 3,957,971 | 5/1976 | Oleniacz ............................. 424/70 |

FOREIGN PATENT DOCUMENTS

| | | |
|---|---|---|
| 843300 | 6/1976 | Belgium ................................. 252/316 |
| 2249552 | 5/1973 | Fed. Rep. of Germany ........... 252/316 |
| 1477048 | 3/1967 | France .................................... 252/351 |

OTHER PUBLICATIONS

Sessa et al.: "Phospholipid Spherules (Liposomes) as a Model for Biological Membranes", Journal of Lipid Research, vol. 9, 1968, pp. 310–318.

Luzzati et al.: "The Structure of the Liquid-Crystalline Phases of Lipid-Water Systems", The Journal of Cell Biology, vol. 12, 1962, pp. 207–219.

Kunitake et al.: "A Totally Synthetic Bilayer Membrane", JACS 99, 3860 (1977).

Tanford: The Hydrophobic Effect: Formation of Micelles and Biological Membranes, a Wiley–Interscience Publ., (1973), pp. 78–79.

Ruckenstein et al.: "Thermodynamics of Amphiphilar Aggregation into Micelles and Vesicles", Micellization, Solubilization, and Microemulsions, vol. 1, Mittal, Plenum Press, (1976), pp. 133–149.

Johnson et al.: "The Opposing Effects of Pressure . . . Permeability of Liposomes of Varying Lipid Composition", Biochim. Biophys. Acta. 307 (1973), pp. 42–57.

Segal et al.: "Liposomes as Vehicles for the Local Release of Drugs", Clinical Science and Molecular Medicine, (1975), 49, pp. 99–106.

Primary Examiner—Richard D. Lovering
Attorney, Agent, or Firm—Cushman, Darby, & Cushman

[57] ABSTRACT

The present invention relates to a process for producing a dispersion of spheres comprising arranged molecular layers encapsulating an aqueous phase. The process comprises admixing a water-dispersible lipid component with the aqueous phase to be encapsulated, the liphophile/hydrophile ratio of the lipid component being such that the lipid swells in the said aqueous phase so as to form a lamellar phase. The lamellar phase is agitated and there is added thereto a dispersion liquid in an amount greater than the resulting lamellar phase and the resulting mixture is vigorously agitated for a period of time ranging from 15 minutes to 3–4 hours. The spheres can encapsulate a water-soluble pharmaceutical, a cosmetic or a food and the dispersions containing said encapsulated materials can be used particularly in the pharmaceutical and cosmetic fields.

9 Claims, No Drawings

COMPOSITIONS CONTAINING AQUEOUS DISPERSIONS OF LIPID SPHERES

This application is a continuation-in-part of our application Ser. No. 700,038, filed June 25, 1976 now abandoned.

It is known that certain lipids possess the ability to form, in the presence of water, mesomorphic phases, the physical state of which is intermediate a crystalline state and a liquid state. Certain known lipids which form a mesomorphic phase swell in an aqueous solution thereby forming spheres which are dispersed in an aqueous medium. These spheres comprise multi-molecular layers, preferably by bimolecular layers, having a thickness approximately 30 to 100 Å (see, in particular, the article of Bangham, Standish and Watkins, J. Mol. Biol., 13, 238 (1965).

Until now, it has only been possible to obtain lipid spheres comprising concentric lamina by using lipids which possess an ionic hydrophilic group and a lipophilic group. Known processes for preparing these spheres involve the production of those having an average diameter less than 1000 Å, and consists of producing a dispersion of the lipid substance which is capable of forming the spheres, and submitting this dispersion to an ultra-sonic treatment. In producing this dispersion which ultimately is submitted to an ultra-sonic treatment, one process comprises producing a thin film, by evaporation, of the lipid substance to be dispersed on a surface and then contacting the thus coated surface with the continuous phase of the desired dispersion and finally agitating the same to provide the dispersion which is then submitted to an ultra-sonic treatment. In another process which is described in French Pat. No. 2,221,122, a dispersion which can ultimately be submitted to an ultra-sonic treatment can be produced by adding the lipid component which forms the surface of spheres to an aqueous phase, then slightly heating and vigorously agitating the mixture in a shaker. The resulting spheres which are made up of concentric layers have a maximum diameter of about 1000 Å and are generally termed liposomes.

In yet another known process for producing liposomes, U.S. Pat. No. 3,932,657 to Rahman, Jan. 13, 1976, teaches the encapsulation of polyaminopolycarboxylic acid chelating agents, EDTA and DTPA, by drying a lipid mixture to form a thin film on the walls of a flask; introducing into the flask a solution of the electrolyte so as to wet the thin lipid film; and shaking the contents of the flask whereby small spherules are formed. Subsequent to the formation of these spherules, i.e. liposomes composed of lipid layers separated by an entrapped aqueous layer containing the said electrolyte, the thus formed suspension of liposomes can be centrifuged with the supernatant being pipetted off, followed by resuspension of the liposomes in normal saline. The same centrifugation and resuspension procedures can be effected on these formed liposomes a plurality of times to insure complete removal of non-encapsulated electrolyte solution.

Heretofore, it has been proposed to employ these liposomes to encapsulate water-soluble active substances in aqueous compartments positioned between adjacent lipid layers thereby protecting the encapsulated active substances against exterior conditions (see, in particular, the article of Sessa and J. Weismann, J. Lipid Res., 9, 310 (1968) and the article of Magee and Miller, Nature, Vol. 235 (1972). See also U.S. Pat. No. 3,957,971 to Oleniacz, May 18, 1976. This patent discloses a liposome which is a matrix of a ternary lipid mixture of 50-80 molar proportions of lecithin, 10-30 molar proportions of dicetyl phosphate and 10-30 molar proportions of a sterol or caprolactam, and an aqueous solution of a humectant disposed interiorly of the liposome which has a substantially continuous outer surface. While known liposomes can vary in size, generally they have a diameter less than 1000 Å. Further, it is known that their ability to penetrate the human body, which thus makes them ideal for numerous pharmaceutical applications, can be varied by altering the exterior electric charge of these liposomes, thereby selectively controlling their fixation site (Biochem. J. (1971), 124 p. 58P). However, the use of these known liposomes in cosmetic preparations has not been favored since the diameter of these liposomes is, as stated before, generally less than 1000 Å and thus they are capable of introducing the products they contain into the body by penetrating the skin. Accordingly, in order to take full advantage of this type of material, it would be desirable to produce spheres of concentric lipid layers having a diameter greater than 1000 Å.

Moreover, the known actual process for obtaining liposomes encapsulating active substances between their concentric lipid layers has considerable drawbacks. In the first place, the active substance which is placed in the continuous phase of the dispersion which is submitted to an ultra-sonic treatment, is only encapsulated between the lipid layers of the liposome in very weak concentrations for only a very small amount of the continuous phase of the dispersion has been found encapsulated between these concentric layers. When it is desired to isolate the encapsulating liposomes, it is necessary to pass the dispersion, which has been submitted to an ultra-sonic treatment, through a "Sephadex" type separation column. In these circumstances, the liposomes have been found to be in the form of an extremely dilute dispersion. From this it results that it is not only practically impossible with known procedures to obtain a strong concentration of liposomes but also it has been observed that the active substance is encapsulated only in weak concentrations, the remainder being lost during elution of the separation columns. While up to now these procedures were necessary to recover the encapsulating liposomes in a simple manner, nonetheless these inefficient procedures were reflected in the high cost of the resulting product. In view of these disadvantages, it has been considered desirable to provide a process for manufacturing spheres with concentric layers from a dispersion having a strong concentration of said spheres whereby any loss of product encapsulated between the layers of the spheres is significantly reduced.

Finally known processes for producing liposomes only utilize certain well defined types of lipids, such as phospholipids or lipids having a hydrophilic ionic group and a lipophilic group, or unsaturated fatty acids. For instance, French application No. 76.02016 discloses a method of preparing a liquid pharmaceutical composition capable of releasing a product at a regulated speed, by uniformly dispersing a phospholipid in water to produce an aqueous dispersion of phospholipid; adding a medicament to this aqueous dispersion of the phospholipid or by dissolving the medicament therein; congealing the thus obtained aqueous dispersion so as to enclose the medicament in the lipid spherules; and then decongealing the cooled dispersion so as to obtain an aqueous suspension of the medicament enclosed in the lipid spheres.

The present invention which overcomes the above disadvantages relates to a process for producing a highly concentrated aqueous dispersion of spheres having a diameter greater or smaller than 1000 Å, the said spheres being capable of encapsulating a high concentration of active substances between the concentric layers of said spheres. In the context of the present invention, the term "encapsulate" is used to indicate that an aqueous phase is confined within the interior of a capsule constituted by the lipid spheres. The process according to the present invention can be applied to ionic or non-ionic lipids and thus enables the use of non-ionic lipid compounds to form these spheres.

The present invention further relates to a novel process for producing a dispersion of spheres constituted by arranged molecular layers encapsulating an aqueous phase comprising admixing at least one liquid water-dispersible lipid having the formula

X—Y wherein X represents a hydrophilic ionic or non-ionic group and Y represents a lipophilic group with an aqueous phase to be encapsulated in the spheres wherein the lipophile/hydrophile ratio of the lipid is such that the lipid swells in the aqueous phase to be encapsulated so as to form a lamellar phase; agitating the resulting mixture so as to assure the production of said lamellar phase; adding a liquid dispersion phase in an amount greater than the quantity of lamellar phase obtained and vigorously shaking the resulting mixture for a period of time ranging from 15 minutes to about 3 hours.

In a preferred embodiment, the weight ratio of the amount of aqueous phase to be encapsulated which is admixed with the lipids, to the amount of lipids forming the lamellar phase is between about 0.1 and about 3; the aqueous phase to be encapsulated within the spheres can be water or an aqueous solution of an active component; the weight ratio of the amount of liquid dispersion phase to the amount of the lamellar phase which is dispersed therein is between about 2 and about 100; the liquid dispersion phase and the aqueous phase to be encapsulated are, preferably, iso-osmotic; the liquid dispersion phase can advantageously be an aqueous solution. The agitation procedures which are effected as the last step of the present process are advantageously effected by means of a shaker agitator. The process is carried out at ambient temperature or at a more elevated temperature if the lipid is solid at ambient temperature. Where it is desired to obtain spheres having an average diameter less than 1000 Å, the resulting dispersion of spheres can be subjected to an ultra-sonic treatment.

To form the lamellar phase, a single lipid material or a mixture thereof can be employed. The lipids employed have a long saturated or unsaturated, branched or linear lipophilic chain having from 12 to 30 carbon atoms such as oleic, lanolic, tetradecylic, hexadecylic, isostearylic, lauric or alkyl phenyl chains. When the hydrophilic group of the lipid forming the lamellar phase is a non-ionic group, a polyoxyethylene, a polyglycerol, a polyol ester, oxyethylenated or not, and, for example, a polyoxyethylenated sorbitol ester, can be employed. When the hydrophilic group of the lipid forming the lamellar phase is an ionic group, advantageously there can be used, as the hydrophilic group, an amphoteric compound having two lipophilic chains or a combination of two long chain organic ions of opposite signs. Very satisfactory results have been obtained by using as the lipids forming the lamellar phase ethers of polyglycerol, such as those which are described in French Pat. Nos. 1,477,048 and 2,091,516 and in the certificate of addition No. 94,928.

The aqueous phase to be encapsulated can include a wide variety of active substances. In particular, pharmaceutically active substances or alimentary substances or cosmetic substances can be employed. Cosmetic substances can include, for instance, components generally employed for the care of the skin and hair, including humectants, such as glycerine, sorbitol, pentaerythritol, inositol, pyrrolidone carboxylic acid and its salts; artificial tanning agents such as dihydroxy acetone, erythrulose, glyceraldehyde and γ-dialdehydes such as tartaric aldehyde, optionally in the presence of dyes; water-soluble anti-solar agents; antiperspirants; deodorants; astringents; skin refreshing products; tonics; cicatrisive products; keratolytic products; depilatories; perfumed water; extracts of animal or vegetable tissue, such as proteins, polysaccharides and amniotic liquid; water-soluble dyes; antipellicular agents; antiseborrheic agents; oxidizing agents (bleaching agents) such as $H_2O_2$; keratin reducing agents such as thioglycolic acid and its salts. Representative active pharmaceutical substances include vitamins; hormones; enzymes, for example, superoxide dismutase; vaccines; anti-inflammatory agents, for example, hydrocortisone; antibiotics; and bactericides.

It is clear that one will select, as a function of the active substance contained in the aqueous phase to be encapsulated, lipids which are capable of encapsulating in a stable manner the desired aqueous phase. To ensure that the lipids which constitute the lamellar phase provide stable spheres, it is necessary that there be sufficient lateral interaction between the lipid chains which, when placed side by side, constitute the layers of the spheres, that is, the Van der Waals forces between the chains must ensure sufficient cohesion between the layers. This condition is satisfied for lipids having the characteristics indicated in the general definition of the process given above. The lipids usefully employed in the process according to the present invention belong to the class of water-in-oil type emulsifying agents.

The process according to the present invention provides dispersions of spheres which are constituted from non-ionic compounds and which, from this fact, form new compositions which enable the encapsulation of active substances, useful for example in pharmacy, in alimentation or in cosmetics. The use of non-ionic compounds as the encapsulating spheres presents a not negligible interest in the case where it is desired to avoid spheres having an electrically charged exterior surface.

The present invention also relates to a new industrial product comprising a dispersion of spheres made from arranged molecular layers of lipid compounds, characterized by the fact that the lipid compounds are non-ionic amphiphilic compounds capable of being dispersed in water, said spheres having a diameter between about 100 and 50,000 Å.

In a preferred embodiment, the spheres of the dispersion according to the present invention encapsulate an aqueous phase; the non-ionic lipid compounds have a lipophile/hydrophile ratio such that the lipid compound swells in the aqueous phase to be encapsulated so as to form a lamellar phase; the hydrophilic groups of the non-ionic lipid compounds are polyoxyethylene groups, polyglycerol groups or esters of polyols, oxyethylenated or not, for example esters of polyoxyethylenated sorbitol; the non-ionic lipid compounds are preferably selected from the group consisting of:

(1) ethers of linear, or branched, polyglycerol having the following respective formulas

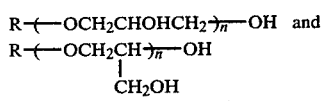

$$R{-}({-}OCH_2CHOHCH_2{-})_n{-}OH \text{ and} \qquad (a)$$
$$R{-}({-}OCH_2CH{-})_n{-}OH$$
$$\qquad\qquad\quad |$$
$$\qquad\qquad CH_2OH$$

wherein n is a whole number between 1 and 6, R is selected from the group consisting of an aliphatic, linear or branched, saturated or unsaturated chain of 12 to 30 carbon atoms, the hydrocarbon radicals of lanolin alcohols and the 2-hydroxy alkyl residue of long chain α-diols;

(2) polyoxyethylenated fatty alcohols;

(3) the esters of polyols, oxyethylenated or not, and, particularly, the esters of polyoxyethylenated sorbitol; and (4) natural or synthetic glycolipids, for example, cerebrosides.

The continuous phase of the dispersion, which surrounds the spheres, is an aqueous phase. The aqueous phase encapsulated within the spheres is an aqueous solution of the desired active substance and is preferably iso-osmotic relative to the continuous phase of the dispersion.

Various additives can be combined with the non-ionic lipid compounds so as to modify its permeability characteristics or the superficial charge of said spheres. Representative additives include long chain alcohols and diols; sterols, for example, cholesterol; long chain amines and their quaternary ammonium derivatives; dihydroxyalkylamines; polyoxyethylenated fatty amines; esters of long chain amino alcohols, their salts and quaternary ammonium derivatives; phosphoric esters of fatty alcohols, for example, sodium dicetyl phosphate; alkylsulfates, for example, sodium cetyl sulfate; certain polymers such as polypeptides; and proteins.

The present invention also relates to a new industrial product comprising a dispersion of spheres made of arranged molecular layers encapsulating an aqueous phase, said layers constituting at least one lipid compound of the formula X—Y, wherein X represents a hydrophilic ionic group and Y represents a lipophilic group, said spheres having a diameter between about 1000 Å and about 50,000 Å.

In a preferred embodiment, the aqueous phase to be encapsulated is an aqueous solution of an active substance; the active substance in the aqueous phase to be encapsulated is a component exhibiting cosmetic activity; the continuous phase of the dispersion is an aqueous phase; the amount by weight of the spheres relative to the weight of the continuous phase of the dispersion is between about 0.01 and 0.5; and the continuous phase of the dispersion is advantageously iso-osmotic relative to the aqueous phase encapsulated within the spheres.

The active substances, which can be encapsulated within the two types of dispersed spheres defined above, are extremely varied and correspond to those which have been indicated above relative to implementing the process of the present invention. Thus, the resulting compositions can be employed in various fields particularly in the pharmaceutical and cosmetic industries.

The latter defined aqueous dispersions are quite desirable in the cosmetic field since the use of large dimensioned spheres substantially reduces or eliminates risk of the passage of these preparations into the body through the skin. Thus, there can be provided, in accordance with the present invention, products useful in the care of the skin and hair, for example, liposomes containing humectants such as glycerin, sorbitol, pentaerythritol, inositol, pyrrolidone carboxylic acid and its salts; artifical bronzing agents such as dihydroxyacetone, erythrulose, glyceraldehyde and γ-dialdehydes such as tartaric aldehyde; skin coloring agents; water-soluble solar filters; antiperspirants; deodorants; astringents; refreshing products; tonics; cicatrisants; keratolytics; depilatories; perfumed water; extracts of animal or vegetable tissue, such as proteins, polysaccharides and amniotic liquids; water soluble hair dyes; antipellicular agents; antiseborrheic agents; oxidizing agents (bleaching agents) such as $H_2O_2$; and reducing agents such as thioglycolic acid and its salts.

It will be noted that the use of aqueous dispersions according to the present invention in cosmetic preparations wherein the dispersions contain non-ionic or ionic lipid compounds provides a considerable advantage relative to the well known use of emulsions. Heretofore, when it was desired to employ preparations containing both fatty bodies and water, it was necessary in order to ensure the stability of the emulsion, to employ an amphiphile emulsifying agent. Further, it was known that certain emulsifying agents can be relatively irritating when applied to the skin. It has been discovered, during the course of work relative to the present invention, that this effect of emulsifying agents, for a given chemical structure, depends considerably on the form under which they are applied to the skin. Thus, it has been found that a water/oil emulsion composed of 42% perhydrosqualene, 8% emulsifying agent and 50% water is strongly irritating, whereas an 8% aqueous dispersion of the same emulsifying agent has a practically insignificant irritation index and that perhydrosqualene is absolutely inoffensive. From this it can be concluded that there is a synergy of irritation when an emulsifying agent is in the presence of an oil phase. The aqueous dispersions according to the present invention avoid the simultaneous use of an emulsifying agent and an oil, and this constitutes an important advance in the cosmetic field.

It will also be noted that there can be added to the dispersions of spheres according to the present invention various auxiliary components so as to modify the appearance or the organoleptic characteristics of the dispersions. Representative auxiliary components include opacifiers, gelling agents, aromatizing agents, perfumes or dyes.

In a general manner, the dispersions according to the present invention are particularly advantageous since they permit the introduction of hydrophilic substances into an essentially lipophilic medium. Under these circumstances, the hydrophilic components are protected from various agents which can alter their nature such as oxidizing agents, digestive juices and more generally those materials which are reactive with the thus encapsulated components. Further, the penetration and/or the fixation of the active substances can be modulated by varying the size of the spheres and their electric charge and their activity can also be deferred, delayed or retarded. Moreover, because they are masked or encapsulated, their organoleptic characteristics, in particular their taste, can be suppressed or sensibly altered. Finally, the lipids employed in these preparations possess, of themselves, such beneficial characteristics or emollient properties, lubricating qualities and lustering power.

Another embodiment of the present invention relates to the production of compositions of the type mentioned above, characterized by the fact that they are a mixture of at least two dispersions of spheres wherein the active substances contained in the aqueous phase encapsulated therein are different.

Advantageously, this embodiment provides a mixed system, i.e. a system where a dispersion of spheres containing a first type of active substances is combined with another dispersion containing a different but compatible or cooperative type of active substance, which permits the two types of substances to act simultaneously at the moment of treatment or use. Such a mixed system optionally provides a synergistic effect which would not be attained if the two types of active substances were employed separately.

In a preferred embodiment, all the spheres of the mixed system are prepared either from an ionic lipid compound or from a non-ionic lipid compound and the active substances contained in the mixture of such spheres are those having cosmetic activity.

Thus, the cosmetic composition according to this embodiment of the invention can result, for example, from a mixture of two dispersions of spheres, wherein the spheres of one dispersion contain in their encapsulated aqueous phase a solar filter and the spheres of the other dispersion contain in their encapsulated aqueous phase a skin coloring agent. As the solar filter, 4-trimethylammonio benzylidene camphor can be employed while the skin coloring agent can be a mixture of dihydroxyacetone and tartaric aldehyde. The said solar filter and the skin coloring agent are encapsulated, separately, in spheres comprised of a non-ionic lipid material of the formula:

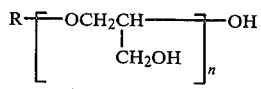

wherein R is hexadecyl and n has a statistical average value of 3.

In yet another embodiment of the present invention, the cosmetic composition can result from a mixture of two dispersions of spheres, wherein the spheres of one dispersion contain in their encapsulated aqueous phase, a solar filter and the spheres of the other dispersion contain in their encapsulated aqueous phase a humectant. Representative solar filter-humectant combinations include (a) an oxyethylenated derivative of para amino benzoic acid, as solar filter, and sodium lactate as humectant wherein these cosmetically active substances are encapsulated, separately, in spheres comprising a non-ionic lipid material of the formula

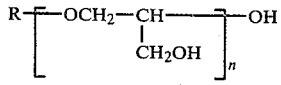

wherein R is hexadecyl and n is a number equal to 2;

(b) an oxyethylenated derivative of para amino benzoic acid, as the solar filter, and the sodium salt of pyrrolidone carboxylic acid, as the humectant, wherein the solar filter can be encapsulated in non-ionic lipid spheres of diglycerol oleate while the humectant can be encapsulated in non-ionic lipid spheres prepared from compounds of the formula

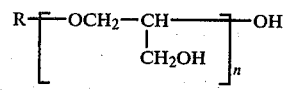

wherein R is hexadecyl and n has a statistical average value of 3; and (c) triethanolamine salicylate, as the solar filter, and the sodium salt of lactic acid, as the humectant, wherein the solar filter and humectant are advantageously encapsulated in ionic lipid spheres prepared, respectively, from hydrogenated egg lecithin and soya lecithin.

It has been observed that the combination of the two dispersions of spheres containing, respectively, a solar filter and a humectant or skin coloring agent provides results superior to those achieved when the two said dispersions are employed separately.

The following non-limiting examples illustrate the present invention.

EXAMPLE 1

In a 50 ml round flask, 500 mg of sorbitol trioleate oxyethylenated with 20 moles of ethylene oxide (sold under the mark "TWEEN 85") are admixed with 0.335 ml of a 0.7 M solution of sorbitol. The resulting mixture is homogenized at ambient temperature.

3 ml of a 1% aqueous solution of polyacrylic acid crosslinked with polyallylsucrose (sold under the mark "CARBOPOL 934") are then added thereto. The flask is then placed on a shaker and is vigorously agitated for 1 hour.

The resulting dispersion is gelled and the diameter of the spheres therein is greater than 1 micron.

EXAMPLE 2

In a 50 ml round flask, 250 mg of oleyl alcohol oxyethylenated with 10 moles of ethylene oxide (sold under the mark "BRIJ 96") are intimately mixed with 250 mg of oleyl alcohol oxyethylenated with 2 moles of ethylene oxide (sold under the mark "BRIJ 92"). To the resulting mixture there is added 1 ml of a 0.5 M solution of glycerol and the resulting admixture is homogenized at ambient temperature.

There are then added 20 ml of a 0.145 M (NaCl, KCl) solution. The flask, placed in a shaker, is vigorously agitated for 1 hour.

The resulting dispersion is fluid and milky and the diameter of the spheres therein is about 1 micron.

EXAMPLE 3

In a 50 ml round flask, 500 mg of a product having the formula

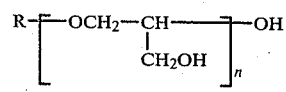

wherein R is the alkyl residue of hydrogenated lanolin alcohols and n has a statistical average value of 3, are mixed with 0.220 ml of a 0.5 M solution of pentaerythritol. The resulting mixture is homogenized at ambient temperature.

There are then added 4 ml of water. The flask, placed on a shaker, is vigorously agitated for 30 minutes.

The resulting dispersion has a milky appearance and the diameter of the spheres therein is greater than 1 micron.

EXAMPLE 4

In a 50 ml round flask 500 mg of a product having the formula

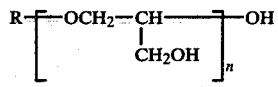

wherein R is tetradecyl and n is 2 is admixed with 0.75 ml of a 0.4 M solution of sorbitol. The resulting mixture is homogenized at 40° C.

There are then added 4 ml of water. The flask, placed on a shaker, is vigorously agitated for 30 minutes.

The resulting dispersion is clear after an ultra-sonic treatment and the diameter of the spheres therein is less than 1 micron.

EXAMPLE 5

In a 50 ml round flask, 500 mg of a product having the formula

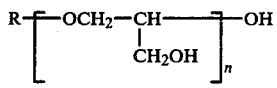

wherein R is hexadecyl and n is 2 are mixed with 0.335 ml of a 0.3 M solution of cysteine. The resulting mixture is homogenized at 55° C.

There are then added 4.1 ml of a 0.14 M (NaCl, KCl) solution. The flask, placed on a shaker, is vigorously agitated for 3 hours.

The resulting dispersion is practically clear at 55° C. The diameter of the spheres contained therein is about 2 microns. On slowly cooling the dispersion to ambient temperature, a white, opaque gel is produced.

The dispersion withdrawn at 55° C. can be diluted with a solution, iso-osmotic or not, containing a thickening agent such as a gum or a polymer to provide a slightly opaque solution. The amount of dilution depends upon the desired appearance of the dispersion.

EXAMPLE 6

In a 50 ml round flask, placed on a water bath maintained at 55° C., 500 mg of a product having the formula

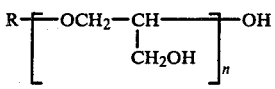

wherein R is hexadecyl and n is 2, are mixed with 10 ml of a 0.3 M solution of methionine. The mixture is homogenized at 55° C.

The flask, placed on a shaker, is vigorously agitated for 3 hours at 55° C.

The resulting dispersion is clear. The diameter of the spheres in the dispersion is about 1 micron. On cooling the dispersion to ambient temperature, a white gel is obtained.

EXAMPLE 7

In a 50 ml round flask, 500 mg of a product having the formula

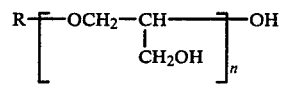

wherein R is the alkyl residue of isostearyl alcohol and n has a statistical average value of 2, are mixed with 5 ml of water. The resulting mixture is homogenized at ambient temperature.

The flask, placed on a shaker, is vigorously agitated for 4 hours.

The resulting dispersion is milky and the diameter of the spheres therein is about 5 microns.

The dispersion can be submitted to an ultra-sonic treatment to reduce significantly the size of the spheres.

EXAMPLE 8

In a 50 ml round flask, 83.2 mg (200 $\mu$-moles) of a product having the formula

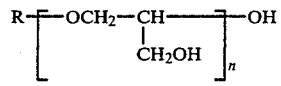

wherein R is the alkyl residue of oleyl alcohol and n is 2, are dissolved in 2 ml of a 2:1 mixture of chloroform and methanol. The solvent is then evaporated with a rotating evaporator and the last remaining traces of the solvent are removed by passage through a blade pump for one hour.

To the above lipid material there are then added 10 ml of a 0.3 M solution of glucose. The flask, placed on a shaker, is vigorously agitated for 4 hours at ambient temperature.

The resulting dispersion is then subjected to an ultrasonic treatment for 20 minutes in order to reduce the diameter of the spheres to a value lower than 0.5 micron. The dispersion is then filtered on a column of coarse Sephadex G50 gel, swollen in a 0.145 M (NaCl, KCl) solution. The resulting dispersion is slightly bluish.

EXAMPLE 9

In a 50 ml round flask, 58 mg of a product having the formula

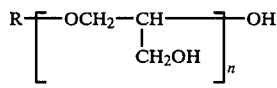

wherein R is the alkyl residue of isostearyl alcohol and n is 2 are intimately mixed with 58 mg of a product having the formula

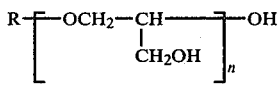

wherein R is the alkyl residue of isostearyl alcohol and n is 6. To the resulting mixture there are added 10 ml of a 1 M solution of glucose at ambient temperature. The flask, placed on a shaker, is vigorously agitated for 4 hours.

The resulting dispersion is very fine and the spheres therein have a diameter of about 1 micron. The dispersion is then subjected to an ultra-sonic treatment for 30 minutes in order to reduce the size of the spheres to a value lower than 0.5 micron.

The dispersions, either that with spheres having a diameter greater than 1 micron or that with spheres having a diameter less than 0.5 micron, are filtered on a column of coarse Sephadex G50 gel swollen in a 0.475 M (NaCl, KCl) solution.

EXAMPLE 10

In a 50 ml round flask, 500 mg of tetraethylene glycol monolauryl ether are mixed with 0.4 ml of a 0.3 M solution of glucose. The resulting mixture is homogenized at ambient temperature.

To the mixture there are then added 5 ml of a 0.145 M (NaCl, KCl) solution. The flask, placed on a shaker, is vigorously agitated for 15 minutes.

The resulting dispersion is clear and the diameter of the spheres therein is about 1 micron.

EXAMPLE 11

In a 50 ml round flask, 500 mg of a product of the formula

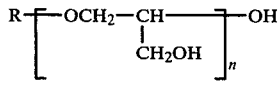

wherein R is hexadecyl and n has a statistical average value of 3 are mixed with 0.5 ml of a solution containing 50 mg/ml of a protein having a molecular weight of about 10,000 and sold under the mark "CROTEINE C". The mixture is homogenized at 60° C. To the homogenized mixture there are added 4 ml of a 0.145 M (NaCl, KCl) solution. The flask, placed on a shaker, is vigorously agitated for 3 hours.

The resulting dispersion is clear and the diameter of the spheres therein is about 1 micron. On slowly cooling the dispersion to ambient temperature, a white opaque gel is obtained.

EXAMPLE 12

In a 50 ml round flask, 300 mg of sphingomyelin are mixed with 0.350 ml of a 0.3 M solution of glucose. The resulting mixture is homogenized at ambient temperature.

There are then added 5 ml of a 0.145 M (NaCl, KCl) solution and the flask, placed on a shaker, is vigorously agitated for 2 hours.

The resulting dispersion is milky and the diameter of the spheres therein is about 2 microns.

The dispersion can be submitted to an ultra-sonic treatment for 1 hour to reduce the diameter of the spheres.

EXAMPLE 13

In a 50 ml round flask, 300 mg of a produce, obtained by molecular distillation, having the formula

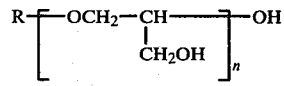

wherein R is the alkyl residue of oleyl alcohol and n is 2, are intimately mixed with 150 mg of cholesterol and 50 mg of an amine of the formula

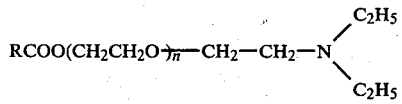

wherein RCOO is the residue of copra and n is a number between 2 and 5. To the resulting mixture there is added 0.5 ml of a 0.3 M solution of sorbitol and the same is then homogenized at ambient temperature.

There are then added 4 ml of a 0.145 M (NaCl, KCl) solution to the homogenous mixture and the flask, placed on a shaker, is vigorously agitated for 4 hours.

The resulting dispersion is opalescent and the diameter of the spheres therein is about 2 microns.

EXAMPLE 14

In a 50 ml round flask, 425 mg of a product having the formula

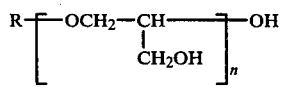

wherein R is the alkyl residue of oleyl alcohol and n is 2, and 75 mg of an amine having the formula

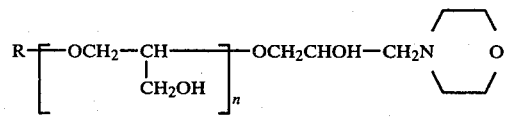

wherein R is oleyl and n has a statistical average value of 1 are mixed with 0.5 ml of a 0.3 M solution of glucose. The resulting mixture is homogenized at ambient temperature.

To the homogeneous mixture there are added 4 ml of a 0.145 M (NaCl, KCl) solution. The flask, placed on a shaker, is vigorously agitated for 4 hours.

The resulting dispersion is opaque and the diameter of the spheres therein is greater than 2 microns.

The dispersion can be submitted to an ultra-sonic treatment to reduce the size of the spheres to less than 1 micron.

EXAMPLE 15

In a 50 ml round flask, 300 mg of sphingomyelin are mixed with 0.350 ml of a 0.3 M solution of ascorbic acid. The resulting mixture is homogenized at ambient temperature.

To the resulting homogeneous mixture there are added 2.650 ml of a 0.145 M (NaCl, KCl) solution. The flask is then placed on a shaker and vigorously agitated for 4 hours.

The resulting dispersion is milky and the diameter of the spheres therein is about 2 microns.

If desired, the dispersion can be filtered on a column of Sephadex G50 corase gel swollen in a 0.145 M (NaCl, KCl) solution.

EXAMPLE 16

In a 50 ml round flask, 142 mg of the sodium salt of $N^2$(alkyl-tallow)-N-dodecyl-N(N',N'-diethylaminoethyl)asparagine are dissolved in 2 ml of a 2:1 mixture of chloroform and methanol. The solvent is evaporated using a rotating evaporator and then the last traces of the solvent are removed by submitting the solution for 1 hour at reduced pressure in a blade pump. There are then added 10 ml of a 0.3 M solution of glucose.

The flask is then placed on a shaker and vigorously agitated for 4 hours at ambient temperature. The size of the spheres in the dispersion is about 1 micron. The dispersion is then filtered on a column of Sephadex G50 coarse gel swollen in a 0.145 M (NaCl, KCl) solution.

EXAMPLE 17

In a 50 ml round flask, 80 mg of a product having the formula

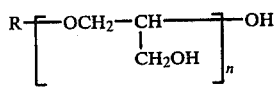

wherein R is hexadecyl and n is 2, 10 mg of cholesterol and 10 mg of dicetyl phosphate are dissolved in 2 ml of a 2:1 mixture of chloroform and methanol. The solvent is then evaporated with a rotating evaporator and the last traces of the solvent are removed by passing the mixture through a blade pump for 1 hour. To this lipid material there are added 10 ml of a 0.15 M solution of the sodium salt of pyroglutamic acid. The flask, placed on a shaker, is vigorously agitated for 2 hours on a water bath maintained at 55° C. Then the same is progressively cooled down to ambient temperature.

The dispersion is submitted to an ultra-sonic treatment for 1 hour at a temperature close to ambient temperature. The dispersion is then filtered on a column of Sephadex G50 coarse gel swollen in distilled water.

The resulting dispersion is fluid and clear after the ultra-sonic treatment and the diameter of the spheres therein is lower than 1 micron.

EXAMPLE 18

In a 50 ml round flask, 240 mg of a product of the formula

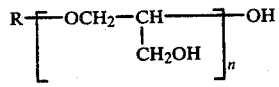

wherein R is the alkyl residue of hydrogenated lanolin and n has a statistical average value of 3 are intimately mixed with 60 mg of cholesterol.

To the resulting mixture there is added 0.4 ml of a 0.15 M solution of the sodium salt of pyroglutamic acid. The mixture is then homogenized at 45° C. To the mixture there are added 4.6 ml of a 0.9% solution of sodium chloride.

The flask, placed in a water bath, is vigorously agitated with a shaker for 2 hours at 45° C. The dispersion is then progressively cooled down to ambient temperature.

The resulting solution is fluid and milky and the diameter of the spheres therein is greater than 1 micron.

EXAMPLE 19

In a 50 ml round flask, 200 mg of a product of the formula

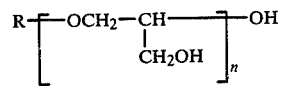

wherein R is hexadecyl and n is 2, 25 mg of cholesterol and 25 mg of dicetyl phosphate are intimately mixed. To the resulting mixture there is added 0.3 ml of a 10% solution of tartaric aldehyde and the same is then homogenized at 55° C. To the resulting homogeneous mixture there are added 4.7 ml of a 0.145 M (NaCl, KCl) solution.

The flask, placed in a water bath, is vigorously agitated with a shaker for 2 hours at 55° C. and then progressively cooled down to ambient temperature.

The resulting dispersion is gelled and has a slightly bluish appearance.

The simultaneous application on the skin of this dispersion of niosomes and an aqueous solution at the same final concentration of tartaric aldehyde, permits to appreciate two effects of the niosomes, i.e. they substantially improve the color developed and they clearly improve the resistance of this coloration to washing with water and detergents.

EXAMPLE 20

In a 50 ml round flask, 300 mg of egg lecithin, 80 mg of cholesterol and 20 mg of dicetyl phosphate are dissolved in 3 ml of a 2:1 chloroform-methanol mixture. The solvent is then evaporated with a rotating evaporator and the last traces of the solvent are removed by passing the mixture through a blade pump for 1 hour. To this lipid material there are added, at a temperature of 40° C., 5 ml of a 4% solution of triethanolamine salicylate. The flask, placed on a shaker, is vigorously agitated for 2 hours at 40° C. and is then progressively cooled down to ambeint temperature. The resulting spherules have a diameter of about 2 microns. If desired, the dispersion containing said spherules can be submitted to an ultra-sonic treatment to reduce the size of the spherules to a value less than 1 micron. The dispersion of spherules can be filtered on a column of Sephadex gel.

EXAMPLE 21

In a 50 ml round flask, 190 mg of a product of the formula

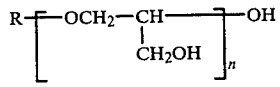

wherein R is the alkyl residue of hydrogenated lanolin alcohols and n has a statistical average value of 3, 100 mg of cholesterol and 20 mg of dicetyl phosphate are dissolved in 3 ml of a 2:1 chloroform-methanol mixture.

The solvent is then evaporated with a rotating evaporator and the last traces of the solvent are removed by passing the mixture through a blade pump. To this lipid material there are added 5 ml of a 8.4% solution of the triethanolamine salt of urocanic acid at a temperature of 70° C. The flask, placed on a shaker, is vigorously agitated for 2 hours at 70° C. Then the same is progressively cooled down to ambient temperature. The resulting fluid dispersion contains spherules having a diameter of about 2 microns.

EXAMPLE 22

In a 50 ml round flask, 154 mg of hydrogenated egg lecithin, 40 mg of cholesterol and 10 mg of dicetyl phosphate are dissolved in 6 ml of a 2:1 chloroform-methanol mixture. The solvent is then evaporated with a rotating evaporator and the last traces of solvent are removed by passing the mixture through a blade pump for 1 hour. To this lipid material there are added 5 ml of a 2% solution of the potassium salt of methoxycinnamic acid at a temperature of 40° C. The flask, placed on a shaker, is vigorously agitated for 2 hours at 40° C. Then the same is progressively cooled down to ambient temperature. The resulting spherules have an average diameter of 5 microns.

EXAMPLE 23

In a 50 ml round flask, 380 mg of a product of the formula

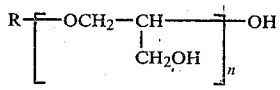

wherein R is hexadecyl and n has a statistical average value of 3, 380 mg of cholesterol and 40 mg of dicetyl phosphate are thoroughly mixed. To this lipid material there are added 3.3 ml of a 4% solution of 4-trimethylammonio benzylidene camphor methyl sulfate. The resulting mixture is homogenized and to the homogeneous mixture there are added 6.7 ml of a 0.9% solution of NaCl at a temperature of 70° C. The flask, placed on a shaker, is vigorously agitated for 2 hours at 70° C. and is then progressively cooled down to ambient temperature. The resulting spheres have an average diameter of 2 microns.

In a separate 50 ml round flask, 180 mg of a product of the formula

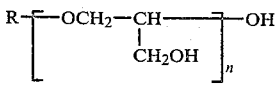

wherein R is hexadecyl and n has a statistical average value of 3, 180 mg of cholesterol and 40 mg of dicetyl phosphate are thoroughly mixed. To this lipid material there are added 0.8 ml of a 3% solution of dihydroxy acetone and 1.5% tartaric acid. The resulting mixture is homogenized and to the homogeneous mixture there are added 4.2 ml of a 0.9% solution of NaCl at a temperature of 70° C. The flask, placed on a shaker, is vigorously agitated for 2 hours at 70° C. and is then progressively cooled down to ambient temperature. The resulting spheres have a diameter of about one micron.

The two dispersions of spheres, thus produced and containing respectively an anti-solar agent and a skin coloring agent, are then admixed with slight agitation, at ambient temperature.

EXAMPLE 24

In a 50 ml round flask, 380 mg of a produce of the formula

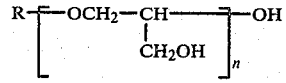

wherein R is hexadecyl and n is equal to 2, 80 mg of cholesterol and 20 mg of dicetyl phosphate are dissolved in 5 ml of a 2:1 chloroform-methanol mixture. The solvent is then evaporated with a rotating evaporator and the last traces of solvent are removed by passing the mixture through a blade pump for 1 hour. To this lipid material there are added at a temperature of 70° C., 5 ml of a 4% solution of paraaminobenzoic acid oxyethylenated with 25 moles of ethylene oxide. The flask, placed on a shaker, is vigorously agitated for 2 hours at 70° C. and then progressively cooled down to ambient temperature. The resulting spheres have an average diameter less than one micron.

Essentially the same procedures noted above are repeated except that the oxyethylenated paraaminobenzoic acid is replaced with sufficient 2% solution of sodium lactate to provide 5 ml of a dispersion containing spheres encapsulating said sodium lactate.

The two dispersions of spheres thus produced are then admixed with slight agitation at ambient temperature.

EXAMPLE 25

In a 50 ml round flask there are mixed 300 mg of diglycerol oleate, 100 mg of cholesterol and 40 mg of dicetyl phosphate. To the resulting mixture there is added 0.6 ml of a 2% solution of paraaminobenzoic acid oxyethylenated with 25 moles of ethylene oxide. This mixture is then homogenized and to the homogeneous mixture there are added 4.4 ml of a 0.9% solution of NaCl at a temperature of 40° C. The flask, placed on a shaker, is vigorously agitated for 2 hours at 40° C. and then progressively cooled down to ambient temperature.

In a separate 50 ml round flask, 166 mg of a product of the formula

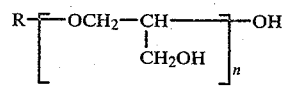

wherein R is hexadecyl and n has a statistical average value of 3, 166 mg of cholesterol and 17 mg of dicetyl phosphate are thoroughly mixed. To this lipid mixture there is added 0.4 ml of a 2% solution of the sodium salt of pyrrolidone carboxylic acid. The mixture is then homogenized and to the homogeneous mixture there are added 4 ml of a 0.9% solution of NaCl at 70° C. The flask, placed on a shaker, is vigorously agitated for 2 hours at 70° C. and then progressively cooled down to ambient temperature.

The two dispersions of spheres thus produced are then admixed with slight agitation at ambient temperature.

EXAMPLE 26

In a 50 ml round flask, 300 mg of hydrogenated egg lecithin, 80 mg of cholesterol and 20 mg of dicetyl phosphate are dissolved in 3 ml of a 2:1 chloroform-methanol mixture. The solvent is then evaporated with a rotating evaporator and the last traces of solvent are removed by passing the mixture through a blade pump for 1 hour. To this lipid material there are added at a temperature of 40° C., 5 ml of a 4% solution of triethanolamine salicylate. The flask, placed on a shaker, is vigorously agitated for 2 hours at 40° C. and then progressively cooled down to ambient temperature.

In a separate 50 ml round flask, 300 mg of soya lecithin, 80 mg of cholesterol and 20 mg of dicetyl phosphate are dissolved in 3 ml of a 2:1 chloroform-methanol mixture. The solvent is then evaporated with a rotating evaporator and the last traces of solvent are removed by passing the mixture through a blade pump for one hour. To this lipid film material there are added 5 ml of a 2% solution of sodium lactate at a temperature of 40° C. The flask, placed on a shaker, is vigorously agitated for 2 hours at 40° C. and then progressively cooled down to ambient temperature.

The two dispersions of spheres thus produced are then admixed with slight agitation at ambient temperature.

The following study is provided to compare the significantly different properties of liposomes obtained from non-ionic materials and those produced from ionic materials. The study also illustrates that the properties of these liposomes can depend on the size of the spheres, it being noted that (a) the permeability of ionic liposomes having a size larger than 1000 Å is greater than the permeability of non-ionic liposomes having the same size; (b) the permeability of ionic liposomes having a size larger than 1000 Å is lower than the permeability of ionic liposomes having a size smaller than 1000 Å; (c) the permeability of ionic liposomes having a size smaller than 1000 Å is greater than the permeability of non-ionic liposomes having the same size; (d) the permeability of the liposomes increases as the time during which the liposomes are subjected to ultrasonic treatment increases; and (e) non-ionic liposomes are capable of encapsulating a greater amount of a given solution to be encapsulated than ionic liposomes of essentially the same size.

In the following study, Parts I and II, the dispersions of the non-ionic and ionic liposomes were prepared by dissolving the respective lipid material in a 2:1 mixture of chloroform and methanol; evaporating the solvent with a rotating evaporator with the last traces thereof being removed by passing the mixture through a blade pump; forming a 3% dispersion of the respective lipid materials in a 0.3 M glucose solution, the dispersing operation being conducted at a temperature greater than the crystallization temperature of the lipid material employed; and cooling the resulting dispersion to ambient temperature with agitation.

Thereafter each dispersion, under a nitrogen atmosphere, was subjected to a conventional ultrasonic treatment for a period of 30 minutes at a temperature greater than the crystallization temperature of the liposome. Subsequently, each liposome dispersion was filtered on a column of Sephadex G50 coarse gel swollen in a 9% NaCl saline solution.

Part I—Permeability Study of Non-ionic and Ionic Liposomes Prepared in Accordance with the Above Procedures In Table I, below, the permeability of the liposomes relative to the encapsulated glucose is based on the amount of glucose passing out through the walls of the liposomes and is expressed by the ratio of free glucose/total glucose and is calculated from dosages of free glucose and total glucose carried out one or several days after the filtration operation. The swelling data indicates the relative amount of glucose encapsulated and is expressed by the ratio of the weight of encapsulated glucose solution to the total weight of the liposomes.

Table I

Nature of Dispersion lipid composition in %

| Non-Ionic Liposome | | | Ionic Liposome | | | | | |
|---|---|---|---|---|---|---|---|---|
| Product of the formula $R-(O-CH_2-CH)_{\overline{n}}-OH$ $\phantom{R-(O-CH_2-}|$ $\phantom{R-(O-CH_2-}CH_2OH$ | | | | | | | | |
| R = hexadecyl n = 2 | 45 | 47.5 | Egg Lecithin | 85 | Egg Lecithin | 75 | Egg Lecithin | 54 |
| cholesterol | 50 | 47.5 | Cholesterol | 10 | Cholesterol | 20 | Cholesterol | 40 |
| Sodium dicetyl-phosphate | 5 | 5 | Sodium dicetyl phosphate | 5 | Sodium dicetyl phosphate | 5 | Sodium dicetyl phosphate | 6 |
| Swelling, % | 93 | 90 | | 87 | | 34 | | 92 |
| Amount of leakage | | | | | | | | |
| 1 hr | 0.02 | 0.24 | | | | 0.40 | | 0.08 |
| 18 hrs. | 0.02 | 0.24 | | 0.52 | | 0.80 | | 0.13 |
| 1 day | 0.35 | | | | | 1.00 | 0.24 | |
| 5 days | 0.05 | 0.35 | | | | 1.00 | | 0.48 |
| 7 days | | | | 1.00 | | 1.00 | | |
| Average size of liposomes | >> 1000Å | ≦ 1000Å | | >> 1000Å * | | ≦ 1000Å | | >> 1000Å * |

*choice between the two formulations

Part II—Permeability Study of Non-Ionic and Ionic Liposomes Prepared in Accordance with the Above Procedures as a Function of Varying Ultrasonic Treatment Times In Table II below, the permeability of the liposomes as a function of the length of time during which they are subjected to a conventional ultrasonic treatment increases as this length of time increases, it being noted, however, that this increase in permeability is significantly greater in the case of ionic liposomes. It will also be noted from the swelling data tabulated below that as the ultrasonic treatment time increases, the non-ionic liposomes, compared to the ionic liposomes, encapsulate more glucose than the ionic liposomes. Moreover it can be seen from this data that the permeability of the liposomes, ionic and non-ionic, is a function of their size, the liposomes with the smaller diameter being more permeable than those having a larger diameter.

Table II

| Ionic Liposome | | |
|---|---|---|
| Egg Lecithin | 85% | |
| Cholesterol | 10% | |
| Sodium dicetyl-phosphate | 5% | |
| Duration of Ultrasonics Minutes | Swelling, % | Amount of Leakage after one day |
| 0 | 76 | 0.6 |
| 5 | 44 | 0.5 |
| 20 | 33 | 1.0 |
| 60 | 21 | 1.0 |

Non-ionic Liposome
Product of the general formula $R-(OCH_2-CH)_{\overline{n}}-OH$
                                                    $|$
                                                    $CH_2OH$

| wherein R = alkyl radical of hydrogenated lanolin alcohols | |
|---|---|
| n, having a statical average value of 3 | 70% |
| Cholesterol | 20% |
| Sodium dicetyl phosphate | 10% |
| Duration of Ultrasonics Minutes | Swelling, % | Amount of Leakage after one day |
| 0 | 80 | 0.0 |
| 20 | 53 | 0.1 |

What is claimed is:

1. A composition comprising a mixture of at least two aqueous dispersions of spheres, each dispersion of spheres comprising arranged molecular layers of a lipid material encapsulating an aqueous phase containing a cosmetically active substance, said lipid material comprising at least one lipid compound having the formula X—Y, wherein Y represents a lipophilic group and X represents a non-ionic hydrophilic group, in which case the diameter of the spheres is between about 100 and 50,000 Å, or an ionic hydrophilic group, in which case the diameter of the spheres is between about 1,000–50,000 Å, the said active substance contained in the encapsulated aqueous phase of the spheres in one of said dispersions being a solar filter and the active substance contained in the encapsulated aqueous phase of the spheres in another of said dispersions being a skin coloring agent.

2. The composition of claim 1 wherein the solar filter is 4-trimethylammonio benzylidene camphor and the skin coloring agent is a mixture of dihydroxyacetone and tartaric aldehyde.

3. A composition comprising a mixture of at least two aqueous dispersions of spheres, each dispersion of spheres comprising comprising arranged molecular layers of a lipid material encapsulating an aqueous phase containing a cosmetically active substance, said lipid material comprising at least one lipid compound having the formula X—Y, wherein Y represents a lipophilic group and X represents a non-ionic hydrophilic group, in which case the diameter of the spheres is between about 100 and 50,000 Å, or an ionic hydrophilic group, in which case the diameter of the spheres is between about 1,000–50,000 Å, the said active substance contained in the encapsulated aqueous phase of the spheres in one of said dispersions being a solar filter and the active substance contained in the encapsulated aqueous phase of the spheres in another of said dispersions being a humectant.

4. The composition of claim 3 wherein the solar filter is an oxyethylenated paraaminobenzoic acid and the humectant is sodium lactate.

5. The composition of claim 4 wherein all the spheres in the said dispersions of spheres are prepared from a non-ionic lipid compound of the formula

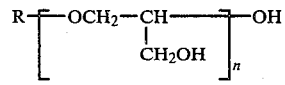

wherein R is hexadecyl and n is a number equal to 2 or 3.

6. The composition of claim 3 wherein the solar filter is oxyethylenated paraaminobenzoic acid and the humectant is the sodium salt of pyrrolidone carboxylic acid.

7. The composition of claim 6 wherein the oxyethylenated paraaminobenzoic acid is encapsulated in spheres of diglycerol oleate and the sodium salt of pyrrolidone carboxylic acid is encapsulated in spheres formed from a non-ionic compound of the formula

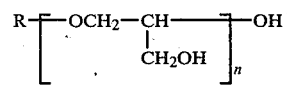

wherein R is hexadecyl and n has a statistical average value of 3.

8. The composition of claim 3 wherein the solar filter is triethanolamine salicylate and the humectant is sodium lactate.

9. The composition of claim 8 wherein the triethanolamine salicylate and the sodium lactate are encapsulated, respectively, in spheres of hydrogenated egg lecithin and spheres of soya lecithin.

* * * * *